United States Patent

Crisalli

[11] 4,272,241
[45] Jun. 9, 1981

[54] METHOD AND ELEMENTS FOR THE FABRICATION OF A PROSTHETIC DENTAL APPLIANCE

[76] Inventor: Emanuel Crisalli, 10724 Baile Ave., Chatsworth, Calif. 91311

[21] Appl. No.: 88,006

[22] Filed: Oct. 25, 1979

[51] Int. Cl.³ .............................................. A61C 13/22
[52] U.S. Cl. ........................................ 433/171; 264/17
[58] Field of Search ............... 433/171, 178, 199, 213, 433/167; 264/17, 19

[56] References Cited

U.S. PATENT DOCUMENTS

| | | | |
|---|---|---|---|
| 3,023,500 | 3/1962 | Prosen | 433/314 |
| 3,218,374 | 11/1965 | Perbohner et al. | 264/17 |
| 3,470,935 | 10/1969 | Prosen | 264/19 |
| 4,017,971 | 4/1977 | Hazar | 433/171 |
| 4,161,065 | 7/1979 | Gigante | 433/214 |

Primary Examiner—Gene Mancene
Assistant Examiner—John J. Wilson
Attorney, Agent, or Firm—Steven P. Brown

[57] ABSTRACT

A method for the fabrication of prosthetic dental appliances such as partials, by which the need for the formation of a refractory model is eliminated. According to the method, a resilient plastic appliance is formed by shaping heat-softenable plastic elements to fit a master model and bonding these elements together with an adhesive. The resultant plastic appliance is then removed from the model and may be used as a permanent appliance or as a model for the casting of a permanent appliance.

27 Claims, 3 Drawing Figures

METHOD AND ELEMENTS FOR THE FABRICATION OF A PROSTHETIC DENTAL APPLIANCE

TECHNICAL FIELD

The present invention relates to the field of fabricating prosthetic dental appliances of the type commonly known as partials. More particularly, the present invention relates to a timesaving method for fabricating dental appliances, and to preformed plastic elements for use in this fabrication, and to permanent plastic appliances formed by the method.

BRIEF DESCRIPTION OF THE PRIOR ART

Dental appliances have been fabricated and used over the past several hundred years. Many methods were used for the fabrication of these appliances, including the carving of the appliance out of a single piece of material, and the forging of the appliance from metal.

More recently, the appliance has been cast in a mold formed from a model of the existing dentition in the mouth of the eventual wearer of the appliance. A relatively reliable and acceptable method for the fabrication of the appliance has been in use for approximately 60 years and is by far the most widely used method in use today.

According to this standard method, an impression of the existing dentition in the wearer's mouth is made using a resilient rubber-like material which is introduced to the patient's mouth in a soft and pliable state and allowed to cure there. This impression is typically made by a dentist in his office. The impression is then sent to a dental lab for fabrication of the appliance. The dental lab first makes a master positive model by pouring plaster into the now cured impression to replicate the existing dentition. After the master model has dried and been mounted in a suitable holder, the appliance is designed and drawn on the model. If necessary, the model is modified by the addition of material where it is not desired for the appliance to be in contact with the existing dentition or tissue in the wearer's mouth. The master model is then duplicated by taking an impression of the master model which, after it cures, is filled with a refractory plaster capable of withstanding high temperatures. The resultant refractory model is then trimmed and the design of the appliance is perfected.

At this point, the actual formation of the first model of the appliance begins. The refractory model of the existing dentition is sprayed with an adhesive agent so that the model of the appliance will stick to the refractory model. A model of the appliance may be formed of bulk wax which is melted and placed on the model with a spatula, or preformed wax or soft plastic parts may be used which are simply placed on the refractory model and bent to fit. The various portions of the appliance model are "welded" together using a hot spatula. After the wax or plastic model of the appliance is finished, the refractory model and the appliance model together are soaked in a release agent and the two models, still bonded together, are invested in a ceramic casting investment. After the investment has hardened, the wax or plastic model of the appliance is burned out in an oven and the actual appliance is formed by forcing hot metal into the now hollow investment. This is commonly done by centrifugal casting.

This prior art method has a number of disadvantages, the primary one being the amount of time required to form the appliance once the original impression of the existing dentition is made. The making of the refractory model is a very time-consuming process, since the impression material used to take an impression of the master model takes about 20 minutes to harden, and the refractory material, which is relatively expensive, takes approximately an hour and a half to harden. More importantly, the trimming and redesigning of the refractory model is a duplication of labor since the master model has already been trimmed and designed. The re-designing of the refractory model is necessary, however, since the impression of the master model is never perfect, and the refractory model, therefore, differs from the master model and must be altered by a skilled technician to be an exact duplicate of the master model.

Beyond the time factor, the prior art method is undesirable in its lack of reliability. There are many steps in the process where unwanted changes in dimension of the models being duplicated can occur, and it is quite common that an appliance formed by this method will not fit in the mouth of the wearer. As a test of the accuracy of the reproduction, it is common practice to test fit the metal appliance on the master model. While this is a fairly reliable indicator of how well the appliance will fit in the wearer's mouth, the metal appliance is much harder than the plaster model and the model is often damaged by the appliance if the appliance is not a perfect fit. If the appliance cannot be trimmed to fit, a new appliance must be cast, but since the master model has been damaged, the chances of the new appliance fitting the mouth of the wearer are greatly reduced.

A final disadvantage of the prior art method is that it can only be done by very skilled technicians. Handfitting of each model along the way must be performed and, due to typical separation between the investment and the refractory model, the metal appliance as cast must be carefully trimmed to remove flashing and other excess material. This is a relatively critical step, since the removal of too much material will render the metal appliance useless and require the repeating of the entire process, starting with the making of the refractory model.

With the proper equipment, a skilled technician could possibly produce one dental appliance by the old method in an eight-hour work day. Typically, a technician works on several appliances in one day and a given appliance is completed two or three days after it is started.

Naturally, due to the amount of labor involved in forming the appliance and the frequent need of remaking appliances, the cost involved in the prior art method is very high.

BRIEF SUMMARY OF THE PRESENT INVENTION

It is, therefore, an object of the present invention to provide a less expensive and more reliable method of fabricating prosthetic dental appliances.

Additionally, it is a further object of the present invention to provide preformed plastic elements for use in the fabrication of the appliances.

It is a third object of the present invention to provide a method in which the first model of the appliance is formed on the master model and in which it is not necessary to form a refractory model.

Finally, it is a further object of the present invention to provide a method by which a permanent appliance may be formed directly on the master model without casting.

According to the method of the present invention, heat-softenable plastic elements are formed to fit the master model and are attached to one another using an adhesive, whereby a resilient plastic model of the appliance is formed directly on the master model. Because the plastic used is strong and resilient at room temperature, the plastic model may be removed from the master model and its fit may be tested in the mouth of the eventual wearer. Any necessary changes may easily be made in the plastic, and when the fit is satisfactory, the plastic model may be invested and a metal appliance cast as in the prior art method. Alternatively, if a sufficiently rigid and tough plastic material is used, a permanent plastic appliance may be formed directly on the master model, thereby eliminating all investment and casting steps.

The primary difference between the present invention and the prior art method is that in the prior art method, the first model of the appliance was made from a soft material such as wax or soft plastic. This has always been thought to be necessary in order to allow proper forming of the model to the extremely close tolerances necessary to assure proper fit of the appliance. However, modern plastics are available which make it possible to heat preformed elements such as clasps, lingual bars, palatal bars, and retention material so that these elements may be exactly fitted to the master model. When these elements cool, they retain their shape. Additionally, modern adhesives are sufficiently strong that these elements may be easily glued together and bonds are formed which are at least as strong as the material itself. Accordingly, it is possible to remove the appliance model from the master model without significant risk of deforming it. In the prior art method, due to the materials used for the appliance model, the appliance model could not be removed from the refractory model for any purpose without completely destroying it. Because of this limitation, it was necessary to invest the appliance model while still on the refractory model on which it was assembled. This is why the refractory model must be formed of a material capable of withstanding the high temperatures encountered in the casting process.

When the method of the present invention is used as a first step in the formation of a metal appliance, the metal casting is of a much higher quality, since the plastic model is invested all at once in a homogeneous investment. This completely eliminates the possibility of separation of the investment resulting in flashing material on the metal casting, thereby reducing the amount of finishing work which must be done to the metal appliance. Also, since the plastic model may be tested in the eventual wearer's mouth, it is very likely that the metal appliance will fit properly.

If a permanent plastic appliance is formed according to the method of the present invention, all casting steps are eliminated and a finished appliance may be formed in one or two hours. A plastic partial has many other advantages, since it may be formed in any color to closely match the tissue against which it will be positioned and since it is far less expensive than the metals typically used in dental appliances. Finally, a plastic partial is far less likely to cause damage to the existing dentition and other tissues in the patient's mouth, since the plastic is easily cleaned and flexible enough to allow natural movement of the dentition and soft enough that it will not wear away the enamel that it is in contact with.

BRIEF DESCRIPTION OF THE DRAWINGS

The present invention will now be described in connection with the attached drawings, in which.

DESCRIPTION OF THE PREFERRED EMBODIMENTS

The method of the present invention results in the formation of a plastic appliance. This appliance may be used as a permanent appliance, or it may be used as a model for the casting of a permanent metal appliance. The steps of the method are as follows:

First, an impression is taken of the existing dentition in the mouth of the eventual wearer of the appliance;

After the impression material has cured, it is filled with a plaster model material in order to make a positive model of the dentition;

After the positive model has hardened, it is removed from the impression material and performed plastic clasps and lingual bars or palatal bars are heat-softened and formed to fit the plaster model;

These plastic elements are bonded together in a predetermined arrangement to form the plastic appliance;

This appliance is then removed from the plaster model and either finished to become a permanent appliance or sprued and invested so that an identical metal appliance may be formed.

Naturally, it is preferred that the plaster model be trimmed and mounted on an appropriate holder prior to assembling the plastic elements, and it is common practice that a model of the mating dentition be attached to a second holder hinged to the first holder and aligned to simulate the alignment of the patient's upper and lower dentition.

In order to facilitate the attachment of the artificial dentition to the appliance, it is advantageous to include "retention" areas on the appliance. Accordingly, when assembling the plastic model of the appliance, preformed plastic retention elements may be bonded to the lingual bar or palatal bar where the artificial dentition will be later added.

Figure 1:
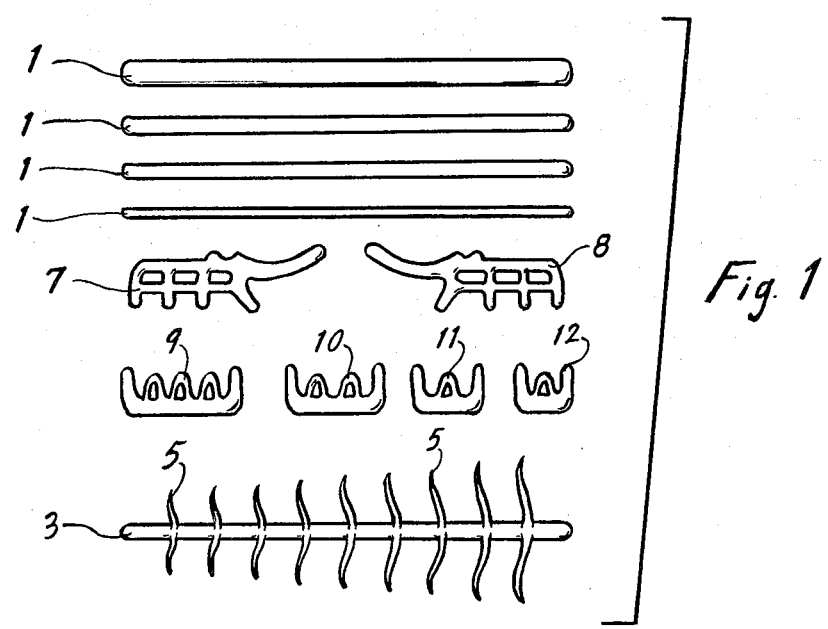
FIG. 1 shows various preformed plastic elements.
Figure 2:
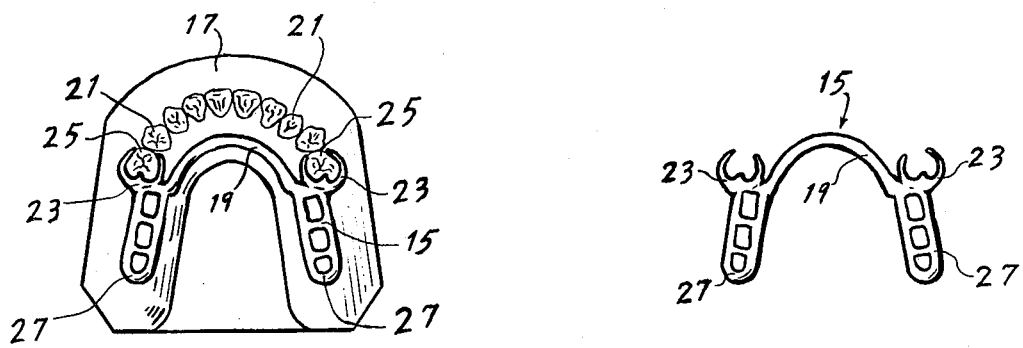
FIG. 2 is a plan view of an assembled plastic appliance or model in place on the master model.

FIG. 1 shows bar segments 1 which can be heat-softened and curved to form palatal or lingual bars. The size of the bar is selected depending upon the width and length of the arch, and the bar is cut to length so that the ends of the bar are adjacent the edentulous areas. The tree 3 includes preformed plastic clasps 5 of various sizes which may be severed from the tree and formed around the anchor tooth on the model by first heating the clasp and then bending it around the tooth. The engaging surfaces of the bar and the clasp are then shaped to form an adequate bonding area and the clasps are bonded to the bar. An appropriately shaped preformed retention element is then chosen from the elements 7, 8, 9, 10, 11, and 12. The retention element is then heated to soften it and it is contoured to fit the existing tissue in the edentulous area. Engagement areas between the retention, the clasp, and the bar are then fitted to provide adequate bonding areas and the retention is bonded to the clasp and the bar. Additional retention may be added at this time, and additional reinforcing members may be added to strengthen the bonds.

The resultant assembled plastic appliance 15 is shown in place on the master plaster model 17. The bar 19 is curved to match the arch of the existing dentition 21 and the clasps 23 are formed to engage the anchor teeth 25. The retention 27 is distributed to provide support for the artificial dentition which will later be added in the edentulous areas.

Figure 3:
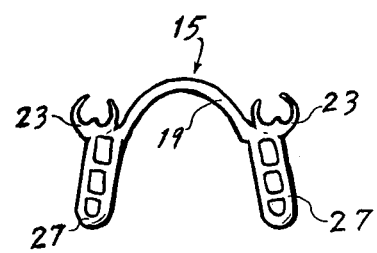
FIG. 3 is a plan view of a finished appliance.

The completed appliance 15 (shown in FIG. 3) is then removed from the model 17 and inspected. If the bonds are complete and no gaps exist between the joined elements, the appliance 15 is positioned over the model 17 to check the fit. If the bar 19 was under a strain when bonded to the clasps, or if the clasps were under a strain when formed around the anchor teeth, the resiliency of these parts will cause them to move when removed from the model. Accordingly, it will be necessary to reheat these parts and make minor adjustments in their shape so that they will perfectly fit the model without the application of any stresses to the parts. Naturally, any misalignment between the clasps and the existing dentition will cause forces to be exerted on the dentition when the appliance is inserted in the mouth of the wearer, and these forces could cause the loosening and loss of the anchor teeth. Any contact point between the bar and the tissue in the mouth could cause extreme discomfort and the development of sores. However, due to the heat-softenable nature of the plastic, these problems can be avoided by fine adjustment and repeated trial of the appliance in the master model.

When the fit of the appliance in the model is satisfactory, the plastic appliance may be tried in the mouth of the wearer. This provides a double check on the quality of the original impression and the formation of the master model from the impression. If the plastic appliance fits the model but does not fit the mouth of the wearer, a second impression is made and a new master model is formed from it. The plastic appliance is then heated and adjusted to properly fit the new master model. The fit of the adjusted appliance may be tested in the mouth of the wearer, and this process may be continued until a perfect fit in the wearer is achieved.

At this point, if a plastic appliance is to be made, the artificial dentition and tissue is bonded to the plastic framework according to conventional methods and the appliance is complete.

If a metal appliance is to be made, the plastic appliance is spured and invested. Since the appliance is not in place on the model when it is invested, the investment is homogeneous and there is no possibility of any flashing forming when the casting is made. After the investment has hardened, the plastic is burned out of the investment in an oven, and molten metal is forced into the hot hollow investment. After the metal has cooled, it is removed from the investment and the sprue is removed. Since there is no flashing, this is the only finishing which must be done to the metal appliance. Since the investment was homogeneous, if the investment and casting procedures were performed properly, the metal appliance will be an exact duplicate of the plastic appliance in every dimension and will properly fit the wearer's mouth.

The artificial dentition and tissue is then attached to the metal appliance framework by the conventional methods.

In order to assure success of the method of the present invention, the plastic elements used must have certain characteristics. As previously mentioned, the elements must be heat-softenable so that they may be easily formed to exactly fit the master model. In order to facilitate the fitting process, the plastics should soften at a temperature of approximately 200° F. so that they may be softened in boiling water or the like. Plastics which soften at this temperature allow use of conventional tools for fitting them when hot and do not pose any threat to damage of the master model. Plastics which soften at appreciably lower temperatures are usable if the plastic appliance is to be used only as an intermediate step for the formation of a metal appliance. Such plastics are not suitable for use in a permanent appliance, since they might become soft and distort in use.

The plastic material must also form a strong bond with the adhesive. This is especially important if the plastic appliance is to be used as the permanent appliance. In this situation, it is also important that the plastic material itself and the adhesive used do not react with the chemicals found in the mouth.

If the plastic appliance is to be used in the formation of a metal appliance, it is important that the plastic material does not expand appreciably when heated to the softening point. Otherwise, the plastic will rupture the investment when the investment is placed in the burn-out oven. Plastics such as styrene, A.B.S. (acrylonitrile butadiene styrene), and polyethylene are suitable for use in the fabrication of a plastic appliance according to the present invention.

These plastics may be colored to match the tissue in the mouth, if desired.

From the foregoing comments, it can be readily realized that the present invention can assume various embodiments. Accordingly, it is to be understood that the present invention is not to be limited by the foregoing description, but is to be limited only by the appended claims.

What I claim is:

1. A method of fabricating a prosthetic dental appliance, said method comprising the steps of:
   taking an impression of existing dentition in the mouth of the eventual wearer of the appliance;
   making a positive model of the dentition from the impression;
   heat softening a resilient preformed plastic bar and resilient preformed plastic clasps;
   fitting the bar and clasps to the positive model in a predetermined arrangement;
   bonding the clasps to the bar to form a plastic dental appliance;
   removing the plastic appliance from the positive model; and
   fabricating a permanent dental appliance using the plastic appliance.

2. The method as claimed in claim 1, further including the steps of:
   heat softening preformed resilient plastic retention material;
   fitting the retention material to the positive model, the bar, and the clasps; and
   bonding the retention material to the bar and clasps.

3. The method as claimed in claim 1 or 2, wherein said fabricating step includes the steps of:
   investing the plastic appliance in casting investment; and
   forming a metal appliance identical to the plastic appliance by an investment casting process.

4. The method as claimed in claim 3, further including the step of attaching artificial dentition to the metal appliance.

5. The method as claimed in claim 3, wherein said heat softening step includes softening the preformed parts without melting by heating the parts to a temperature above the softening point of the parts, but below the melting point thereof.

6. The method as claimed in claim 5, wherein the parts are softened by heating to a temperature in the range of 180°–240° F.

7. The method as claimed in claim 6, wherein said heat softening step includes immersing the parts in heated sand.

8. The method as claimed in claim 5, wherein the parts are softened by heating to a temperature in the range of 180°–212° F.

9. The method as claimed in claim 8, wherein said heat softening step includes immersing the parts in heated water.

10. The method as claimed in claim 3, wherein said fitting step includes:
bending the bar to fit the curvature of the existing dentition as represented on the positive model;
bending the clasps to fit respective, preselected, anchor teeth as represented on the positive model; and
forming mutually engaging bonding areas on the bar and the clasps.

11. The method as claimed in claim 3, further comprising the step of test fitting the plastic appliance in the mouth of the eventual wearer subsequent to said removing step and prior to said fabricating step.

12. The method as claimed in claim 11, further comprising the step of reheat-softening portions of the removed plastic partial and bending the reheat-softened portions to make the plastic appliance fit the mouth of the eventual wearer.

13. The method as claimed in claim 1 or 2, wherein said fabricating step includes attaching artificial dentition and tissue to the plastic model.

14. The method as claimed in claim 13, wherein said heat softening step includes softening the preformed parts without melting by heating the parts to a temperature above the softening point of the parts, but below the melting point thereof.

15. The method as claimed in claim 14, wherein the parts are softened by heating to a temperature in the range of 180°–240° F.

16. The method as claimed in claim 15, wherein said heat softening step includes immersing the parts in heated sand.

17. The method as claimed in claim 14, wherein the parts are softened by heating to a temperature in the range of 180°–212° F.

18. The method as claimed in claim 17, wherein said heat softening step includes immersing the parts in heated water.

19. The method as claimed in claim 13, wherein said fitting includes:
bending the bar to fit the curvature of the existing dentition as represented on the positive model;
bending the clasps to fit respective, preselected, anchor teeth as represented on the positive model; and
forming mutually engaging bonding areas on the bar and the clasps.

20. The method as claimed in claim 13, further comprising the step of test fitting the plastic appliance in the mouth of the eventual wearer subsequent to said removing step and prior to said fabricating step.

21. The method as claimed in claim 20, further comprising the step of reheat-softening portions of the removed plastic partial and bending the reheat-softened portions to make the plastic appliance fit the mouth of the eventual wearer.

22. The method as claimed in claim 13, further comprising the step of coloring the preformed parts to match the tissue of the eventual wearer's mouth.

23. The method as claimed in claim 2, wherein the preformed bar, clasps and retention material are formed from one of the plastics from the group consisting of styrene, acrylonitrile butadiene styrene and polyethylene.

24. The method as claimed in claim 1, wherein the preformed bar and clasps are formed from one of the plastics from the group consisting of styrene, acrylonitrile butadiene styrene and polyethylene.

25. A method of fabricating a prosthetic dental appliance to fit the existing dentition in the mouth of the eventual wearer, said method comprising the steps of:
making a positive model of the existing dentition;
heat softening without melting preformed resilient clasps, retention material, and a bar formed of one of the plastics of the group consisting of styrene, acrylonitrile butadiene styrene, and polyethylene;
fitting the heat softened clasps, retention material, and bar to the positive model;
bonding the fitted clasps, retention material, and bar together to form a plastic appliance fitted on the model; and
removing the appliance from the model.

26. A prosthetic dental appliance framework comprising:
at least two clasps;
a curved bar arching between said clasps; and
retention material attached to said bar and said clasps, said clasps, bar, and retention material being formed of a resilient heat-softenable plastic having a softening point in the range of 180°–250° F., whereby said clasps, bar, and retention material may be heat softened and shaped to fit a model representative of the existing dentition of an eventual wearer's mouth and subsequently may be cooled below the softening point and removed from the model without distortion.

27. The framework as claimed in claim 26, wherein said plastic is selected from the group consisting of styrene, acrylonitrile butadiene styrene, and polyethylene.

* * * * *